United States Patent
Sugiura et al.

(10) Patent No.: US 6,337,414 B1
(45) Date of Patent: Jan. 8, 2002

(54) PROCESS FOR PRODUCING PARTIAL GLYCERIDE

(75) Inventors: Masakatsu Sugiura; Masami Shimizu; Yasushi Yamada; Kouji Mine; Eizo Maruyama; Naoto Yamada, all of Ibaraki (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/743,218

(22) PCT Filed: Jul. 6, 1999

(86) PCT No.: PCT/JP99/03632

§ 371 Date: Jan. 8, 2001

§ 102(e) Date: Jan. 8, 2001

(87) PCT Pub. No.: WO00/03031

PCT Pub. Date: Jan. 20, 2000

(30) Foreign Application Priority Data

Jul. 9, 1998 (JP) .......................................... 10-194237

(51) Int. Cl.$^7$ ................................................. C07C 51/43
(52) U.S. Cl. ....................................... 554/174; 435/134
(58) Field of Search ........................... 554/174; 435/134

(56) References Cited

FOREIGN PATENT DOCUMENTS

| JP | 60/102192 | * | 6/1985 |
| JP | 62/201091 | * | 5/1987 |
| JP | 06/343481 | * | 2/1994 |
| JP | 08/214892 | * | 8/1996 |

* cited by examiner

*Primary Examiner*—Deborah D. Carr
(74) *Attorney, Agent, or Firm*—Oblon, Spivak, McClelland, Maier & Neustadt, P.C.

(57) ABSTRACT

The invention relates to a process for preparing a partial glyceride, which includes, in a glycerolysis reaction of oil or fat making use of a lipase, conducting the reaction in the presence of water under conditions that crystals are partially precipitated in the reaction system in the course of the reaction and the concentration of free fatty acids in an oil phase amounts to at least 5% by weight.

3 Claims, No Drawings

PROCESS FOR PRODUCING PARTIAL GLYCERIDE

This application is a 371 of PCT/JP99/03632 filed Jul. 6, 1997.

TECHNICAL FIELD

The present invention relates to a preparation process of partial glycerides making good use of a glycerolysis reaction of oil or fat by a lipase.

BACKGROUND ART

Preparation processes of partial glycerides include an esterification process and a glycerolysis process, and each process includes cases making use of a chemical catalyst and cases making use of an enzyme catalyst. As an esterification process making use of an enzyme catalyst, there has been known a process in which partial glycerides are prepared from oleic acid or the like high in fatty acid purity and glycerol as described in Japanese Patent Publication No. 56311/1994 and Japanese Patent Application Laid-Open No. 19090/1987. However, this process is not preferable as the preparation process of the partial glycerides from the economical point of view because a fatty acid prepared by decomposing oil or fat at a high temperature and a high pressure and then removing a colored component by a distilling treatment is used, and glycerol obtained by dehydration, concentration of purification treatments of an about 10% aqueous solution of glycerol produced upon the decomposition of the oil or fat is used. Accordingly, the glycerolysis process in which both fatty acid group and glycerol group constituting the partial glycerides are derived from a cheap oil or fat, and a deficient glycerol group can be supplied as glycerol is effective as the industrial production process of the partial glycerides.

The processes for preparing the partial glycerides from such a cheap oil or fat and glycerol by an enzymatic glycerolysis reaction are reported in Japanese Patent Publication No. 12710/1992, JAOCS, 71, 3, 339 (1994), etc.

However, the process described in Japanese Patent Publication No. 12710/1992 requires a special lipase satisfying conditions under which no secondary production of free fatty acids in a low water content region is attendant, so that it is difficult to preset a water content in a reaction system and procure the lipase. On the other hand, in the process described in JAOCS, 71, 3, 339 (1994), the partial glycerides are prepared from hydrogenated hardened beef tallow and glycerol by a glycerolysis process by which the formation of fatty acids is inhibited. However, this process has involved a problem that reproducibility of the reaction is poor.

Accordingly, it is an object of the present invention to provide a process for preparing a partial glyceride with industrial advantage by an enzymatic glycerolysis reaction.

DISCLOSURE OF THE INVENTION

The present inventors have found that when in a glycerolysis reaction of oil or fat making use of an easily available lipase, the reaction is conducted in a system in which water is present, under conditions that the secondary production of fatty acids occurs to a great extent and that crystals are precipitated in the reaction system, which are entirely different from the usual common sense, the yield of a partial glyceride, particularly a diglyceride is enhanced with great strides, thus leading to completion of the present invention.

According to the present invention, there is thus provided a process for preparing a partial glyceride, which comprises, in a glycerolysis reaction of oil or fat making use of a lipase, conducting the reaction in the presence of water under conditions that crystals are partially precipitated in the reaction system in the course of the reaction and the concentration of free fatty acids in an oil phase amounts to at least 5% by weight.

According to the present invention, there is also provided a process for preparing a diglyceride, which comprises conducting a removing operation of fatty acid, glycerol and monoglyceride components from a reaction mixture in the reaction described above or after completion of the reaction.

BEST MODE FOR CARRYING OUT THE INVENTION

In the present invention, oil or fat, a lipase, glycerol and water are used as raw materials. Examples of the oil or fat include vegetable oils and animal oils, more specifically, soybean oil, rapeseed oil, cotton-seed oil, corn oil, rice oil and fish oil. Oil or fat, in which a proportion of saturated fatty acids in the acyl group is at most 30% by weight, is preferably used. When the content of the saturated fatty acids is high, not only a high temperature is required of the reaction, but also a reaction product cannot be taken out of a vessel after the reaction, or heating is required, and so handling is complicated because the melting point of the raw oil or fat itself is high and the melting point of a partial glyceride formed is higher. In addition, a problem of deactivation of the enzyme arises in the high-temperature and high-water content system.

No particular limitation is imposed on the lipase used. However, an enzyme (1,3-position-selective lipase") specifically acting on the 1- and 3-positions of glycerol is preferred. More preferably, lipases derived from microorganisms of the genera Rhizopus, Aspergillus and Mucor, and splenic lipases, more specifically, lipases derived from *Rhizopus delemar, Rhizopus japonicus, Rhizopus niveus, Aspergillus niger, Mucor javanicus* and *Mucor miehei* may be used. Immobilized lipases obtained by immobilizing each of the lipases on various kinds of carriers (Celite, diatomaceous earth, silica gel, ion-exchange resin, etc.) may also be used. In general, the use of the latter lipases, i.e., (heat-resistant) immobilized lipases having high durability in a wide concentration range is preferred to the use of the former lipases. Many of these lipases or immobilized lipases are easily available as products on the market. The amount of the lipase used is preferably 0.1 to 30% by weight, particularly 1 to 15% by weight (200 to 100,000 units per g of oil or fat) based on the raw materials for the reaction.

No particular limitation is imposed on the water content in the process according to the present invention. However, it is preferably 5 to 50% by weight, particularly 8 to 30% by weight, in terms of an initial concentration in the reaction system, based on glycerol from the viewpoint of acceleration of the reaction. With the progress of the reaction, the water content in the reaction system somewhat varies. However, the reaction is scarcely affected thereby.

Fatty acids and partial glycerides may exist in the raw materials for the reaction in addition to the oil or fat, glycerol and water. However, the number of moles of glycerol group is preferably controlled to a range of 0.3 to 3, particularly 0.8 to 1.5 per mole of the fatty acid group in the whole raw material.

The reaction conditions in the present invention require that crystals are partially precipitated in the reaction system in the course of the reaction and the concentration of free fatty acids in an oil phase amounts to at least 5% by weight. The conditions under which crystals are partially precipitated in the reaction system in the course of the reaction are conditions that oil or fat to be reacted is naturally melted in the initial stage of the reaction, but parts of monoglycerides and free fatty acids formed with the progress of the reaction are precipitated.

Thus, it is assumed that both of monoglycerides and free acids are partly excluded from the phase system of the reaction when brought in the condition under which a part of crystals is precipitated in the course of the reaction, whereby the glycerolysis reaction is further accelerated. Such conditions vary according to the oil or fat used as a raw material. When oil or fat, in which a proportion of saturated fatty acids in the acyl group is at most 30% by weight, is used as the oil or fat, the conditions are preferably achieved by presetting the reaction temperature to a range of 0 to 250° C., particularly 0 to 150° C.

In the present invention, the conditions are preset in such a manner that the concentration of free fatty acids in an oil phase amounts to at least 5% by weight, preferably 8 to 30% by weight, the yield of the partial glycerides is enhanced with great strides. Such conditions are preferably achieved by presetting the reaction temperature to a range of 0 to 25° C., particularly 0 to 15° C. like the conditions for the precipitation of crystals.

The fact that the yield of the partial glycerides is enhanced by the presetting of these reaction conditions is contrary to the idea of the conventional processes described in Japanese Patent Publication No. 12710/1992 and the like that conditions that the water content is low and no free fatty acid is formed are preset. This is considered to be attributable to the fact that the conventional view of glycerolysis reaction mechanism have been wrong. More specifically, the glycerolysis reaction of oil or fat (TG) with glycerol have generally been considered to be as follows. Namely, a fatty acid group in the oil or fat is bonded to glycerol (GLY) to form monoglycerides (MGs) and diglycerides (DGs) as shown in the following scheme. The water content in the reaction system at this time is considered to be a factor that the enzymatic activity (reaction rate) is changed. Namely, the reaction has been considered to be an ester exchange reaction or alcoholic group exchange reaction in which no fatty acid is formed.

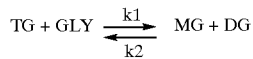

However, when an experiment of the glycerolysis reaction is conducted, hydrolysis occurs even in a region of a trace water content to form fatty acids. Even when the rate equations of the respective components are calculated out from the above formula to conduct kinetic analysis, the presence of the fatty acids formed cannot be theoretically proven. The reaction of a lipase has generally been considered to take place at an interface between an oil phase and a water phase. However, this cannot be explained since the reaction occurs even in a nonaqueous system containing no water.

Therefore, the reaction mechanism of the glycerolysis in the case where a 1,3-position-selective lipase is used as an enzyme catalyst is considered to be as follows. Namely, no alcohol group (ester) exchange reaction takes place, and hydrolysis, ester synthesis, conversion into MG and conversion into DG only take place. A reaction site is considered to be a contact point between the oil phase and the enzyme, and the concentrations of the respective components in the rate equation are regarded as concentrations in the oil phase. More specifically, it has been considered that the concentrations of the fatty acids and glycerides constituting the oil phase, and the concentration of dissolved water and GLY contribute to the reaction, while water and GLY potion in the aqueous solution phase of glycerol do not contribute to the reaction and only affect the concentrations of water and GLY in the oil phase. When experimental data were subjected to fitting (numerical analysis) using simultaneous differential equations of the rate equation on such hypothesis, the calculated result consisted with the experimental date with considerable accuracy. When the experimental results at various temperature in a range in which no crystal was precipitated were also subjected to numerical analysis to calculate out respective rate constants. These values were Arrhenius-plotted against the temperatures. As a result, linearity is obtained. Therefore, the validity of the model was able to be proven, and so it is considered that the glycerolysis reaction progresses in accordance with the following scheme.

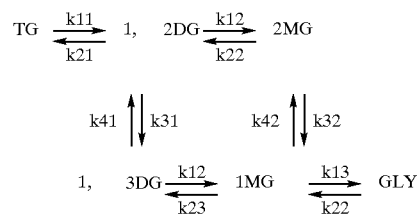

More specifically, the mechanism that partial glycerides is formed from oil or fat and glycerol using an enzyme as a catalyst is considered to be as follows. Namely, TG is hydrolyzed to form DGs and fatty acids, the fatty acids and GLY are subjected to ester synthesis to form MGs, and further esterification occurs to synthesize DGs. Such elucidation of the mechanism of the glycerolysis permits proving that the yield of the partial glycerides is enhanced.

As described above, the reaction temperature is preferably suitably adjusted according to the kind of the resin used at a temperature range of 0 to 25° C. (particularly 0 to 15° C.), and the reaction time is suitably 10 to 200 hours, particularly 20 to 100 hours.

The reaction may be further continued after removing the crystals precipitated in the course of the reaction outside the system. However, the crystals may be removed after completion of the reaction. In order to collect the partial glycerides from the reaction mixture, it is preferable to conduct the above crystal-removing operation, water phase- (GLY phase-) removing operation and distilling operation in suitable combination.

In order to obtain diglycerides in the process according to the present invention, it is only necessary to conduct the removing operation of the fatty acid, glycerol and monoglyceride components from a reaction mixture. Parts of the fatty acid and monoglyceride components can be removed by the crystal-removing operation. Water, glycerol and lipase can be removed by the water phase-removing operation. The fatty acids, monoglycerides and glycerol in the oil phase can be efficiently removed by distillation, particularly molecular distillation. Accordingly, these operations are combined, whereby the intended product (diglyceride concentration: at least 55% by weight, triglyceride concentration: at most 30% by weight) high in diglyceride content can be obtained.

EXAMPLES

The present invention will hereinafter be described by the following Examples.

Examples 1 to 5 and Comparative Examples 1 to 6

A 4-necked flask was charged with raw oil or fat (100 g), lipase powder (3 g; or 30 g in the case of an immobilized lipase), water (0 to 3 g) and glycerol (21 g; water content in glycerol: 0.150%) to conduct a reaction for 72 hours with stirring at 450 rpm in a thermostatic chamber controlled at 5 to 45° C. (Table 1). The contents were in the form of a liquid-liquid emulsion of an oil phase and an aqueous solution of glycerol up to about 2 hours from the beginning of the reaction. In Examples and Comparative Examples, 1, 2 and 6, however, white crystals were gradually precipitated after that, and a slurry state, in which the crystals were present, was held until the reaction was completed.

After completion of the reaction, the reaction mixture containing the crystals was heated to 70° C. to melt the crystals, and centrifugation (3,000 rpm, 5 minutes) was then conducted. As a result, the reaction mixture was separated into two phases. An upper layer separated is an oil phase (A) in which a triglyceride (TG), diglycerides (DGs), monoglycerides (MGs), fatty acids (FAs), soluble glycerol (GLY) and soluble water were present, and a lower layer was an aqueous solution of glycerol containing the enzyme. In the analysis of the oil phase, a concentration of the fatty acids was calculated out from an acid value and an average molecular weight, and concentrations of TG, DG, MG and GLY by trimethylsilylating them and then correcting each peak area obtained by using gas chromatography from the peak area of a standard sample of its corresponding pure product. The water content was determined by the Karl Fischer's method. The results are shown in Table 2.

After completion of the reaction, the reaction mixture was subjected to ultracentrifugation (40,000 rpm, for 1 hour) at the same temperature as the reaction temperature. As a result, the reaction mixture was separated into an upper layer which was a transparent oil phase (B) containing no crystal and a lower layer which was a mixture of the enzyme, a crystal portion and an aqueous solution of glycerol. As analyses of the oil phase (B), in addition to the same analysis as in the oil phase (A), compositional analysis of fatty acids (alkyl) was conducted by hydrolyzing the oil phase (B), then conducting methyl esterification and using gas chromatography, thereby determining the amount of saturated fatty acids. The results are shown in Table 3.

Further, the oil phase (B) was subjected to a molecular distillation treatment under conditions of 240° C. and 6.45 Pa to concentrate DG into the residual portion, thereby analyzing the compositions of glyceride and alkyl. The results are shown in Table 4.

Further, the residual portion is charged into a plastic container (PET bottle), and the plastic container was transferred to a thermostatic chambers controlled at 5° C. and 15° C., respectively, thereby observing the degree of precipitation of crystals. The results are shown in Table 5.

In the reactions in all of Examples, and Comparative Examples 1, 2 and 6, crystals were precipitated in the course of the respective reactions.

In Comparative Examples 3, 4 and 5, no crystal was precipitated, and so ultracentrifugation was not conducted.

TABLE 1

|  | Raw oil or fat | Amount of oil or fat | Amount of glycerol | Water | Enzyme species | Amount of enzyme | Temp. |
|---|---|---|---|---|---|---|---|
| Ex. 1 | Soybean oil | 100 g | 21 g | 3 g | PL | 3 g | 5° C. |
| Ex. 2 | Soybean oil | 100 g | 21 g | 3 g | IM | 30 g | 5° C. |
| Ex. 3 | Soybean oil | 100 g | 21 g | 3 g | PS | 3 g | 5° C. |
| Ex. 4 | Rapeseed oil | 100 g | 21 g | 3 g | PL | 3 g | 5° C. |
| Ex. 5 | Lard | 100 g | 21 g | 3 g | PS | 3 g | 45° C. |
| Comp. Ex. 1 | Soybean oil | 100 g | 21 g | 0 g | IM | 30 g | 5° C. |
| Comp. Ex. 2 | Soybean oil | 100 g | 21 g | 0.3 g | PL | 3 g | 5° C. |
| Comp. Ex. 3 | Soybean oil | 100 g | 21 g | 3 g | PL | 3 g | 40° C. |
| Comp. Ex. 4 | Soybean oil | 100 g | 21 g | 3 g | IM | 30 g | 40° C. |
| Comp. Ex. 5 | Rapeseed oil | 100 g | 21 g | 3 g | PL | 3 g | 40° C. |
| Comp. Ex. 6 | Beef Tallow | 100 g | 21 g | 0.8 g | PS | 3 g | 45° C. |

Water content in the raw glycerol: 0.15%
PL: Lipase PL (Alcaligenes sp.; product of Meito Sangyo Co., Ltd.)
IM: Lipozyme IM (*Mucor miehei*, product of Novo Nordisk Bioindustry Co.)
PS: Lipase PS (*Psedomonas fluorescens*; product of Amano Pharmaceutical Co., Ltd.)

Water content in the raw glycerol: 0.15%

PL: Lipase PL (Alcaligenes sp.; product of Meito Sangyo Co., Ltd.)

IM: Lipozyme IM (Mucor miehei, product of Novo Nordisk Bioindustry Co.)

PS: Lipase PS (Psedomonas fluorescens; product of Amano Pharmaceutical Co., Ltd.)

TABLE 2

| | Composition (% by weight) of Oil Phase (A) after completion of the reaction | | | | | |
|---|---|---|---|---|---|---|
|  | Fatty acid | GLY | MG | DG | TG | DG/(DG + TG) × 100 |
| Ex. 1 | 15.9 | 5.2 | 33.9 | 37.3 | 7.7 | 82.9 |
| Ex. 2 | 17.9 | 2.0 | 24.5 | 43.2 | 12.6 | 77.4 |
| Ex. 3 | 14.4 | 2.7 | 27.7 | 41.2 | 14.0 | 74.6 |
| Ex. 4 | 18.4 | 7.0 | 27.8 | 35.7 | 11.1 | 76.3 |
| Ex. 5 | 14.2 | 2.4 | 27.7 | 41.0 | 14.7 | 73.6 |
| Comp. Ex. 1 | 1.3 | 0.1 | 1.9 | 9.9 | 86.8 | 10.2 |
| Comp. Ex. 2 | 4.5 | 6.4 | 39.5 | 32.1 | 21.5 | 59.9 |
| Comp. Ex. 3 | 14.1 | 1.6 | 13.0 | 41.5 | 29.8 | 58.2 |
| Comp. Ex. 4 | 12.9 | 0.7 | 13.3 | 38.6 | 34.5 | 52.8 |
| Comp. Ex. 5 | 14.3 | 1.5 | 13.7 | 39.5 | 31.0 | 56.0 |
| Comp. Ex. 6 | 4.7 | 5.5 | 25.1 | 39.9 | 24.8 | 61.7 |

TABLE 3

Composition of Oil Phase (B) after removing crystals

| | Fatty acid | GLY | MG | DG | TG | Composition of alkyl, C16 + C18 |
|---|---|---|---|---|---|---|
| Ex. 1 | 19.5 | 3.3 | 26.9 | 41.0 | 9.3 | 4.6 |
| Ex. 4 | 19.9 | 3.6 | 24.2 | 39.1 | 13.2 | 2.7 |
| Ex. 5 | 16.8 | 1.8 | 22.1 | 43.7 | 15.6 | 30.9 |
| Comp. Ex. 3* | 14.1 | 1.6 | 13.0 | 41.5 | 29.8 | 14.8 |
| Comp. Ex. 5* | 14.3 | 1.5 | 13.7 | 39.5 | 31.0 | 5.3 |
| Comp. Ex. 6 | 5.2 | 4.2 | 22.3 | 40.6 | 27.7 | 44.6 |

The composition of the oil phase (A) in Comparative Examples because no crystal was precipitated.
C16 = Palmitic acid,
C18 = Stearic acid.

The composition of the oil phase (A) in Comparative Examples because no crystal was precipitated. C16=Palmitic acid, C18=Stearic acid.

TABLE 4

Composition of residue after molecular distillation treatment

| | Fatty acid | GLY | MG | DG | TG | Composition of alkyl, C16 + C18 |
|---|---|---|---|---|---|---|
| Ex. 1 | 0.1 | 0.0 | 1.2 | 74.8 | 23.9 | 3.3 |
| Ex. 4 | 0.1 | 0.0 | 1.3 | 70.1 | 28.5 | 2.2 |
| Ex. 5 | 0.2 | 0.0 | 1.4 | 66.7 | 31.7 | 27.8 |
| Comp. Ex. 3 | 0.2 | 0.0 | 1.6 | 52.2 | 46.0 | 14.9 |
| Comp. Ex. 5 | 0.1 | 0.0 | 1.1 | 51.4 | 47.4 | 5.2 |
| Comp. Ex. 6 | 0.1 | 0.0 | 1.2 | 55.7 | 43.0 | 41.2 |

TABLE 5

Low-temperature preservation test of residue

| | After 24 hrs. at 15° C. | After 24 hrs. at 5° C. |
|---|---|---|
| Ex. 1 | Transparent liquid having flowability | Transparent liquid having flowability |
| Ex. 2 | Transparent liquid having flowability | Transparent liquid having flowability |
| Comp. Ex. 3 | Precipitate Sedimented; only upper part had flowability | Having no flowability due to crystallization as a whole, and not taken out of the bottle |
| Comp. Ex. 5 | Precipitate Sedimented; only upper part had flowability | Having no flowability due to crystallization as a whole, and not taken out of the bottle |

From the above results, it was proven that in the preparation of the partial glycerides by the glycerolysis reaction of oil or fat with a lipase, (1) the yield is more enhanced when water is present in the reaction system, (2) the yield is more enhanced under conditions that crystals are precipitated in the course of the reaction and the content of free fatty acids in an oil phase is high, and (3) the collection and purification of the partial glycerides become difficult unless the reaction is conducted under high-temperature conditions when lard or the like high in saturated fatty acid content is used, while handling becomes easy and purification can be easily conducted even under low-temperature conditions when oil or fat low in saturated fatty acid content is used.

INDUSTRIAL APPLICABILITY

According to the present invention, high-purity partial glycerides can be produced with industrial advantage under mild conditions.

What is claimed is:

1. A process for preparing a partial glyceride, which comprises, in a glycerolysis reaction of oil or fat making use of a lipase, conducting the reaction in the presence of water under conditions that crystals are partially precipitated in the reaction system in the course of the reaction and the concentration of free fatty acids in an oil phase amounts to at least 5% by weight.

2. The process according to claim 1 for preparing a diglyceride, wherein the removing operation of the fatty acid, glycerol and monoglyceride components is at least one operation selected from (1) a removing operation of crystals precipitated in the reaction system in the reaction, (2) a removing operation of a water phase and (3) a distilling operation.

3. The process according to claim 1 or claim 2 for preparing the partial glyceride, wherein oil or fat, in which a proportion of saturated fatty acids in the acyl group is at most 30% by weight, is used as the raw oil or fat.

* * * * *